US00PP22245P3

(12) United States Plant Patent
Ludvik

(10) Patent No.: US PP22,245 P3
(45) Date of Patent: Nov. 15, 2011

(54) CHERRY TREE NAMED 'KORVIK'

(50) Latin Name: *Pruntus avium*
Varietal Denomination: Korvik

(76) Inventor: Vaclav Ludvik, Horice (CZ)

( * ) Notice: Subject to any disclaimer, the term of this patent is extended or adjusted under 35 U.S.C. 154(b) by 0 days.

(21) Appl. No.: 12/460,904

(22) Filed: Jul. 23, 2009

(65) Prior Publication Data

US 2010/0043110 P1 Feb. 18, 2010

Related U.S. Application Data

(60) Provisional application No. 61/137,623, filed on Jul. 31, 2008.

(51) Int. Cl.
*A01H 5/00* (2006.01)

(52) U.S. Cl. ..... Plt./181

(58) Field of Classification Search ..... Plt./181
See application file for complete search history.

(56) References Cited

OTHER PUBLICATIONS

GTITM UPOVROM Citation for 'Korvik' as per CZ PBR application filing No. 1327; Dec. 20, 2001.*
GTITM UPOVROM Citation for 'Korvik' as per CZ NLI application filing No. 6558; Dec. 20, 2001.*

* cited by examiner

*Primary Examiner* — Kent L Bell
(74) *Attorney, Agent, or Firm* — Ballew Law

(57) ABSTRACT

'Korvik' is a new and distinct cherry variety (*Prunus avium*) notable for its round shape and resistance to cracking. 'Korvik' is further notable for its productivity on dwarfing rootstocks, and tolerance to Monilia disease ("brown rot").

2 Drawing Sheets

Latin name of the genus and species of the plant claimed: *Prunus avium.*
Variety denomination: 'Korvik'.

STATEMENT REGARDING FEDERALLY SPONSORED RESEARCH OR DEVELOPMENT

None.

BACKGROUND AND SUMMARY OF THE VARIETY

'Korvik' originated in 1973 as a result of a controlled cross of 'Kordia' (female parent) and 'Vic' (male parent) cherry trees. Asexual propagation by budding was first carried out in 1975 in East Bohemia, Czech Republic. The variety has since been observed over a number of asexually propagated generations, and has been found to remain true to type.

'Korvik' is a new and distinct cherry variety notable for its round shape and resistance to cracking. 'Korvik' is further notable for its productivity on dwarfing rootstocks, and tolerance to Monilia disease ("brown rot"). 'Korvik' is more upright than its parent 'Kordia' which is more spreading and has less number of lenticels on the tree stem than its parent 'Vic'. The duration of the flowering of 'Korvic' is 1-2 days longer than its parent 'Vic'. In addition, 'Korvik' differs from parental varieties by leaf shape. The leaf margin of 'Korvik' is obtuse serrate, whereas the leaf margin of its parent, 'Kordia', is acute serrate.

BRIEF DESCRIPTION OF THE PHOTOGRAPHS

Figure 1:
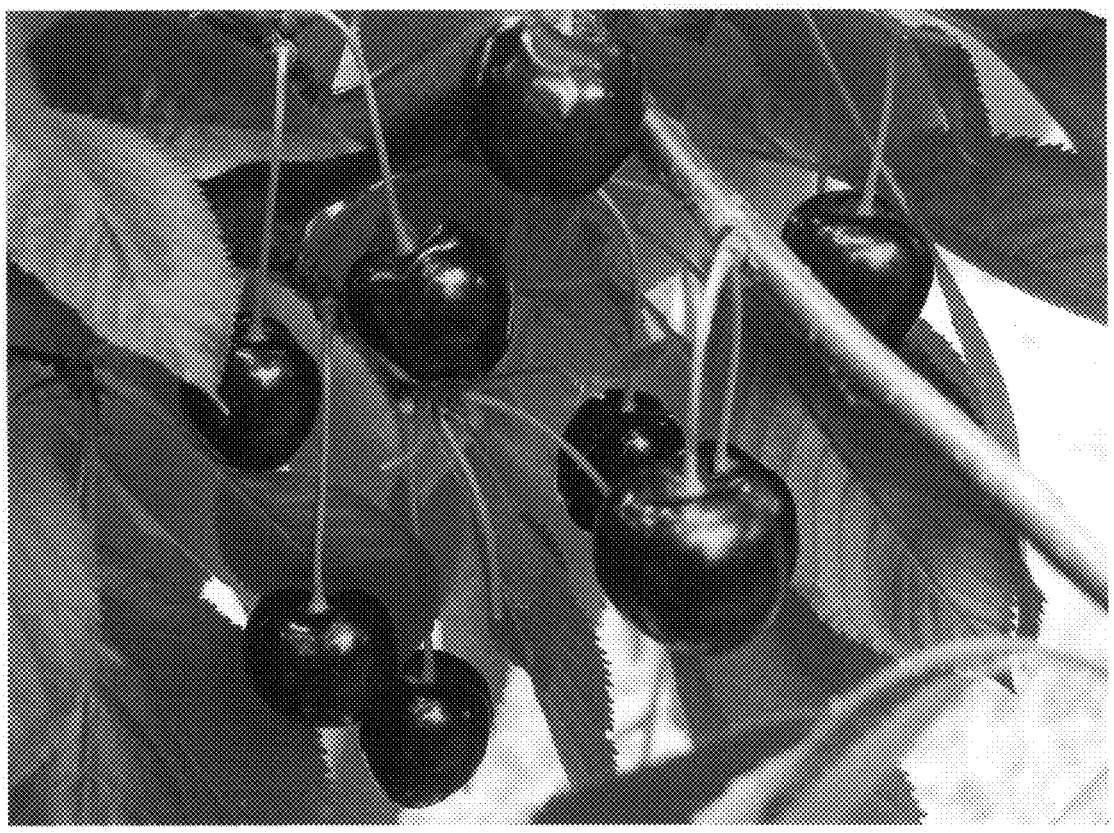
Figure 2:
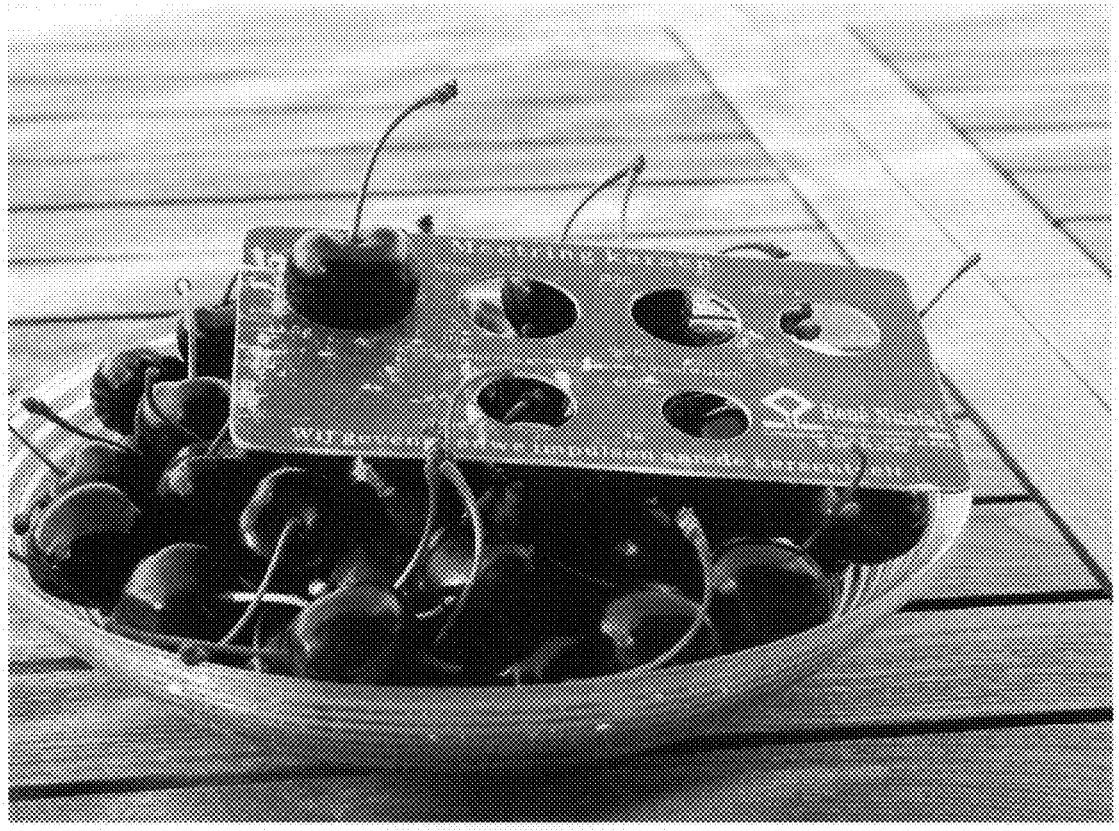

FIG. 1 shows the fruit and leaves of 'Korvik'; and
FIG. 2 shows the fruit of 'Korvik'.

DETAILED BOTANICAL DESCRIPTION

The following detailed botanical description is based on observations of 'Korvik' cherry trees grown at East Bohemia, Czech Republic. Color descriptions refer to The Royal Horticultural Society Colour Chart. It should be understood that the characteristics described will vary somewhat depending upon cultural practices and climatic conditions, and can vary with location and season. Quantified measurements are expressed as an average of measurements taken from a number of individual plants of the new variety. The measurements of any individual tree, or any group of trees, of the new variety may vary from the stated average.

Tree:

*Size.*—Height: 3.9 m; Diameter 2.2 m.
*Form.*—Conical.
*Vigor.*—Medium.
*Hardiness.*—High.
*Trunk.*—Diameter: 96 mm at 0.5 m above ground; Texture: Medium smooth; Lenticels: very few in number; Color: greyed orange 165B.
*Branches.*—Scaffold branch length: 0.8 m; Diameter: 24 mm; Texture: smooth; Color: brown 200B; Number of lenticels per $cm^2$: 4-5; Lenticel length: 2-3 mm; Lenticel diameter: 1 mm; Lenticel color greyed orange 165B; Fruiting branch length: 0.6 m; Diameter: 8.5 mm; Texture: smooth; Color: brown 200B; Number of lenticels per $cm^2$: 7; Lenticel length: 1 mm; Lenticel diameter: 0.5 mm; Lenticel color: greyed orange 165B; Current season branch length: 0.6 m; Texture: smooth; Color: greyed orange 177B; Number of lenticels per $cm^2$: 6; Lenticel length: 0.3 mm; Lenticel diameter 0.3 mm; Lenticel color: greyed orange 175B.

Leaf:

*Size.*—Length: 105 mm; Width: 62 mm.
*Shape.*—Oval; Apex: pointed; Base: obtuse.
*Margin.*—Obtuse serrate.

*Texture.*—Upper surface: glossy; Lower surface: dull with marked veining.
*Color.*—Upper surface: green 136B; Lower surface: green 137C.
*Petiole.*—Length: 22 mm; Diameter: 0.4 mm; Color: greyed purple 183B.

Leaf glands:
*Size.*—Length: 1 mm; Width: 0 8 mm.
*Shape.*—Oval.
*Number per leaf.*—1-2.
*Location.*—Mostly on the petiole, upper position.
*Color.*—Greyed purple 183A.

Flower buds:
*Size.*—Length: 6.5 mm; Diameter: 3.2 mm.
*Shape.*—Conical.
*Number on each fruiting spur.*—2.5.
*Color.*—Greyed purple 166A.
*Blooming period.*—14 days.
*Date of full bloom.*—Medium late (April 22).

Flowers:
*Petal size.*—Length: 15 mm; Width: 12 mm.
*Petal number.*—5 per flower.
*Petal shape.*—Oval; Apex: rounded; Base: slightly pointed.
*Petal margin.*—Smooth.
*Petal texture.*—Upper surface: slight venous; Lower surface: nearly smooth.
*Petal color.*—Upper surface: white N155A; Lower surface: red-purple 69C.

Sepals:
*Size.*—Length: 6 mm; Diameter: 4 mm.
*Number.*—5.
*Shape.*—Widely conical; Apex: pointed.
*Margin.*—Smooth.
*Texture.*—Upper surface: dull smooth; Lower surface: glossy smooth.
*Color.*—Upper surface: Yellow green 147B; Lower surface: green 138B.
*Peduncle length.*—36 mm; Diameter: 1 mm; Color: green 137B.

Reproductive characteristics:
*Nectary color.*—Yellow 2C.
*Stamen number.*—16.
*Filament color.*—Red-purple 69C.
*Anther shape.*—Round to oval.
*Anther size.*—Length: 0.5 mm; Diameter: 0.5 mm.
*Anther color.*—Yellow orange 14A.
*Pollen amount.*—Medium.
*Pollen color.*—Yellow orange 14A.
*Carpel style length.*—12 mm.
*Carpel style color.*—Yellow green 145D.
*Style color.*—Yellow green 145C.
*Stigma shape.*—Oval.
*Stigma diameter.*—0.6 mm.
*Stigma color.*—Yellow green 145B.

Fruit:
*Size.*—Large; Height: 27.2 mm; Suture diameter: 28.3 mm; Apex diameter: 22.7 mm; Stem cavity: Medium, Depth: 2-2.5 mm, Breadth 10-11 mm; Peduncle: Length 48-55 mm, diameter 1.3-1.5 mm, Color: Green 146C; Quantity of fruit per cluster: 2-4.
*Fruit shape.*—Round; Base shape: Round to oval.
*Skin.*—Color: Greyed purple 187B; Thickness: Medium, limited tendency to cracking.
*Flesh.*—Color Greyed purple 187D; Flesh Texture: Above mean 6 (if the rating scale from 1 worst to 9 best is used); Flesh Fiber: Medium; Flavor: Medium, slightly acidulated sweet; Aroma: Good; Eating quality: Good; Brix: Varies from 16.2° to 20.6°.
*Stone.*—Size: Length 12.5 mm, Width 10.5 mm at its widest point near the center; Form: Oblong; Sides: Ridges 4-6 with varying amounts of encircling the sutures of the pit; No tendency to pit cracking; Color Orange white 159A; Kernal size; Length 8.9 mm, Width at widest point: 5.6 mm; Kernel color: Orange 22A.
*Firmness.*—Medium; It was measured by Durofel DTT 100 Agrotechnologie SA-Licence CTIFL (Digital Firmness Tester France); Its scale values ranged from 0-99 where 85=4.5 kg/0.5 $cm^2$ of penetrometer measurement; Mean value of 'Korvik' was 69.
*Fruit weight.*—2nd Year after planting: 0.25 kg; $3^{rd}$ Year after planting 1 kg; $4^{th}$ Year after planning: 5 kg.
*Time of ripening.*—Late.
*Harvest.*—Started on July $11^{th}$ in 2010 in East Bohemia, Czech Republic.

Orchard performance:
*Disease resistance/tolerance.*—Tolerant to Monilia and *Blumeriella jaapii* infection.
*Yield.*—Very good yields on dwarf rootstocks.

I claim:

1. A new and distinct cherry tree substantially as shown and described herein.

* * * * *